(12) United States Patent
Hayashi et al.

(10) Patent No.: US 10,905,893 B2
(45) Date of Patent: Feb. 2, 2021

(54) METHOD OF CONTROLLING DEFIBRILLATOR WITH FUNCTION OF ANALYZING ELECTROCARDIOGRAM, AND DEFIBRILLATOR

(71) Applicant: NIHON KOHDEN CORPORATION, Tokyo (JP)

(72) Inventors: Satoshi Hayashi, Tokyo (JP); Tsutomu Wakabayashi, Tokyo (JP); Hideo Ozawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 14/046,686

(22) Filed: Oct. 4, 2013

(65) Prior Publication Data

US 2014/0100497 A1    Apr. 10, 2014

(30) Foreign Application Priority Data

Oct. 5, 2012  (JP) ................................ 2012-223601
Jul. 31, 2013  (JP) ................................ 2013-158834

(51) Int. Cl.
*A61N 1/39* (2006.01)
*A61N 1/36* (2006.01)
(Continued)

(52) U.S. Cl.
CPC ........ *A61N 1/3987* (2013.01); *A61B 5/04012* (2013.01); *A61H 31/00* (2013.01);
(Continued)

(58) Field of Classification Search
CPC . A61N 1/3611; A61N 1/3625; A61B 5/04012
(Continued)

(56) References Cited

U.S. PATENT DOCUMENTS 7,463,922 B1 * 12/2008 Snyder et al. ................ 607/5
8,744,573 B2 * 6/2014 Freeman ....................... 607/5
(Continued)

FOREIGN PATENT DOCUMENTS

CN    102048531 A    5/2011
EP    1 491 176 A1    12/2004
(Continued)

OTHER PUBLICATIONS

Unai Irusta et al.; "A Least Mean-Square Filter for the Estimation of the Cardiopulmonary Resuscitation Artifact Based on the Frequency of the Compressions"; IEEE Transactions on Biomedical Engineering; vol. 56, No. 4, Apr. 2009; pp. 1052-1062.
(Continued)

*Primary Examiner* — Rex R Holmes
*Assistant Examiner* — Jennifer L Ghand
(74) *Attorney, Agent, or Firm* — Kenealy Vaidya LLP

(57) ABSTRACT

A method of controlling a defibrillator with a function of analyzing an electrocardiogram, includes: dividing an electrocardiogram of a patient into a plurality of analysis zones; executing analysis of the electrocardiogram in each of the divided analysis zones; based on a result of the analysis of the electrocardiogram in each of the analysis zones, executing determination whether electric shock on the patient is necessary or not, and calculating reliability of the determination; and based on a combination of the determination and the reliability, instructing a first procedure to be performed on the patient.

24 Claims, 9 Drawing Sheets

(51) Int. Cl.
    *A61B 5/04*      (2006.01)
    *A61N 1/362*     (2006.01)
    *A61H 31/00*     (2006.01)
    *A61B 5/0295*    (2006.01)
    *A61N 1/365*     (2006.01)
    *A61B 5/053*     (2006.01)
    *A61B 5/083*     (2006.01)

(52) U.S. Cl.
    CPC .......... *A61N 1/3611* (2013.01); *A61N 1/3625* (2013.01); *A61B 5/0295* (2013.01); *A61B 5/053* (2013.01); *A61B 5/083* (2013.01); *A61N 1/36521* (2013.01)

(58) Field of Classification Search
    USPC ...................................... 600/508–509; 607/7
    See application file for complete search history.

(56) References Cited

U.S. PATENT DOCUMENTS

| | | |
|---|---|---|
| 2004/0267324 A1 | 12/2004 | Geheb et al. |
| 2006/0011203 A1 | 1/2006 | Myklebust |
| 2006/0025825 A1 | 2/2006 | Bowers |
| 2006/0149157 A1 | 7/2006 | Weil et al. |
| 2006/0173500 A1 | 8/2006 | Walker et al. |
| 2009/0171230 A1 | 7/2009 | Yamaguchi et al. |
| 2011/0105930 A1 | 5/2011 | Thiagarajan et al. |
| 2011/0202100 A1* | 8/2011 | Tan ..................... A61H 31/005 607/6 |
| 2016/0015991 A1* | 1/2016 | Firoozabadi ......... A61B 5/7221 607/7 |

FOREIGN PATENT DOCUMENTS

| | | |
|---|---|---|
| EP | 2 074 943 A1 | 7/2009 |
| EP | 2 319 409 A1 | 5/2011 |
| JP | 2002-119490 A | 4/2002 |
| WO | 2011/100534 A1 | 8/2011 |
| WO | WO 2013/179234 | * 12/2013 |

OTHER PUBLICATIONS

Tobias Werther et al.; "CPR Artifact Removal in Ventricular Fibrillation ECG Signals Using Gabor Multipliers"; IEEE Transactions on Biomedical Engineering; vol. 56, No. 2, Feb. 2009; pp. 320-327.
The extended European Search Report for the related European Patent Application No. 13187490.1 dated Jan. 8, 2014.
The European Office Action for the related European Patent Application No. 13187490.1 dated Jan. 30, 2015.
Japanese Office Action for the related Japanese Patent Application No. 2013-158834 dated Jan. 4, 2017.
Chinese Office Action for the related Chinese Patent Application No. 201310465311.0 dated Dec. 1, 2016.
Japanese Office Action for the related Japanese Patent Application No. 2013-158834 dated Aug. 8, 2017.
Japanese Report of Reconsideration by Examiner before Appeal 2013-158834 dated Dec. 6, 2017.

* cited by examiner

FIG. 7

|  | DURING INTERRUPTION OF PROCEDURE | MIXTURE | DURING PROCEDURE |
|---|---|---|---|
| NUMBER OF DETERMINATIONS THAT APPLICATION OF DEFIBRILLATION IS NECESSARY | i | j | k |
| NUMBER OF DETERMINATIONS THAT APPLICATION IS NOT NECESSARY | l | m | n |

METHOD OF CONTROLLING DEFIBRILLATOR WITH FUNCTION OF ANALYZING ELECTROCARDIOGRAM, AND DEFIBRILLATOR

CROSS-REFERENCE TO RELATED APPLICATION(S)

This application is based upon and claims the benefit of priority from prior Japanese patent applications No. 2012-223601 filed on Oct. 5, 2012 and No. 2013-158834 filed on Jul. 31, 2013, the entire contents of which are incorporated herein by reference.

BACKGROUND

The presently disclosed subject matter relates to a defibrillator with a function of analyzing an electrocardiogram.

In a life-saving procedure, continuous implementation of chest compression is a critical factor in successfully saving the life of a patient in cardiac arrest. For a cardiac arrest patient who experiences ventricular fibrillation or pulseless ventricular tachycardia, also delivery of electric shock constitutes a critical factor in successfully saving the patient. In a guideline for a life-saving procedure, therefore, it is requested to alternately perform cardiopulmonary resuscitation (hereinafter, abbreviated as CPR) by chest compression, artificial ventilation, or the like, and electric shock.

Electric shock is a medical practice in which, in order to treat a fatal arrhythmia, a large current is caused to flow into the heart of a patient. When electric shock is applied to a person who is not necessary to undergo electric shock, there arises the possibility that a fatal arrhythmia occurs. Therefore, it is requested that, before application of electric shock, an electrocardiogram is analyzed to surely determine whether the patient experiences ventricular fibrillation or ventricular tachycardia or not. In order to perform accurately and surely the determination based on the electrocardiogram analysis, it is preferable from the viewpoint of preventing noise contamination that the rescuer interrupts chest compression and separates from the patient.

Particularly, therefore, an automated external defibrillator (hereinafter, abbreviated as AED) which is to be used by an ordinary person without knowledge of reading of an electrocardiogram is requested to have a high accuracy of an analysis of an electrocardiogram. When an electrocardiogram is to be analyzed, consequently, an AED instructs the operator to separate from the patient, and an electrocardiogram which is not contaminated with noises is analyzed, thereby realizing a high analysis accuracy which is necessary in an international standard (IEC-60601-2-4).

In order to successfully save the life of a patient in cardiac arrest, however, continuous implementation of chest compression is important, and it is not preferable from the viewpoint of saving of the life of the patient that the rescuer interrupts the chest compression, even though the interruption is conducted in order to surely analyze an electrocardiogram. For the purpose of further satisfying these requirements, therefore, it is preferable to shorten the interruption time of chest compression.

Therefore, a technique has been proposed in which, in order to shorten the interruption time of chest compression, an electrocardiogram is analyzed during, for example, CPR. Non-patent Document 1 below discloses a technique in which noises in CPR are removed to enhance the accuracy of an electrocardiogram analysis during CPR.

(Non-patent Document 1) IEEE TRANSACTIONS ON BIOMEDICAL ENGINEERING, VOL. 56 NO. 4, APRIL 2009

In the technique disclosed in Non-patent Document 1 above, however, it is difficult to obtain an analysis accuracy which is equivalent to that of an analysis that is performed while the operator separates from the patient or under noise-free conditions, because of irregularity of noises which are caused to contaminate an electrocardiogram by chest compression. In the electrocardiogram analysis during CPR which is disclosed in Non-patent Document 1, namely, it is difficult to correctly determine whether electric shock is necessary or not. In order to satisfying a high analysis accuracy which is requested in the international standard, therefore, the rescuer must analyze an electrocardiogram in a state where the rescuer interrupts chest compression and separates from the patient. As a result, the interruption time of chest compression cannot be shortened.

SUMMARY

The presently disclosed subject matter may provide a defibrillator with a function of analyzing an electrocardiogram, and a defibrillator in which, while maintaining a high analysis accuracy, the interruption time of chest compression can be shortened.

The method of controlling a defibrillator with a function of analyzing an electrocardiogram, the method may comprise: dividing an electrocardiogram of a patient into a plurality of analysis zones; executing analysis of the electrocardiogram in each of the divided analysis zones; based on a result of the analysis of the electrocardiogram in each of the analysis zones, executing determination whether electric shock on the patient is necessary or not, and calculating reliability of the determination; and based on a combination of the determination and the reliability, instructing a first procedure to be performed on the patient.

In a process of executing the analysis of the electrocardiogram in each of the analysis zones, whether or not a first waveform indicating that the electric shock is necessary or a second waveform indicating that the electric shock is not necessary is contained may be detected in the electrocardiogram in each of the analysis zones, and, in a process of executing the determination and calculating the reliability, based on a number of detections of the first waveform or the second waveform, the determination whether the electric shock on the patient is necessary or not may be executed, and the reliability of the determination may be calculated.

The method may further comprise: classifying a life-saving procedure state of the patient in each of the analysis zones. In a process of executing the determination and calculating the reliability, based on the classified life-saving procedure state of the patient in each of the analysis zones, and the result of the analysis of the electrocardiogram in each of the analysis zones, the determination whether the electric shock on the patient is necessary or not may be executed, and the reliability of the determination may be calculated.

The life-saving procedure state of the patient may be classified into: a state of during procedure in which a second procedure is performed on the patient; a state of during interruption of procedure in which a second procedure is interrupted; and a state which includes both the state of during procedure and the state of during interruption of procedure.

The second procedure may include chest compression.

The life-saving procedure state of the patent may be classified based on at least one of: a thoracic impedance; a frequency characteristic of the electrocardiogram; an amplitude of the electrocardiogram; an amplitude of a capnograph; and a signal acquired from an electrode attached to an operator who performs the chest compression.

The second procedure may include artificial ventilation.

The life-saving procedure state of the patient may be classified based on at least one of a thoracic impedance and a capnograph.

The reliability of the determination may be calculated based on reliability determination information including at least one of: information indicating whether or not the electrocardiogram has an analysis zone, which is classified as the state of during interruption of procedure; information indicating whether or not results of analysis in a plurality of analysis zones, which are classified as the state of during procedure, coincide with each other; and information indicating whether or not, in all analysis zones, an amplitude of the electrocardiogram is within a preset measurable range.

The reliability of the determination may be calculated based on reliability determination information including at least one of: information indicating whether or not a period of the chest compression is constant; and information indicating whether or not a large variation exists in a result of frequency analysis of the electrocardiogram during the chest compression.

The first procedure may include at least one of: an implementation of electric shock; a continuation of a procedure based on cardiopulmonary resuscitation; a check of a pulse; and an implementation of electrocardiogram analysis.

The method may further comprise, after a process of instructing the first procedure to be performed on the patient, executing analysis of an electrocardiogram of the patient which is measured while instructing the first procedure; when a procedure determined from a result of the analysis coincides with the first procedure, continuing instructing the first procedure; and when a procedure determined from a result of the analysis does not coincide with the first procedure, changing the first procedure to a third procedure.

The third procedure may include at least one of an abort of electric shock, and an implementation of reanalysis.

In the electrocardiogram divided into the analysis zones, the electrocardiogram measured in a latest time period and contained in latest zones of the analysis zones may be set as an analysis target.

The defibrillator with a function of analyzing an electrocardiogram, the defibrillator analyzing the electrocardiogram during a procedure based on cardiopulmonary resuscitation, the defibrillator may comprise: a cardiopulmonary resuscitation instructing section which is configured to instruct an operator on a start and end of the procedure based on cardiopulmonary resuscitation; an electrocardiogram analyzing section which is configured to: divide an electrocardiogram of a patient into a plurality of analysis zones; execute analysis of the electrocardiogram in each of the divided analysis zones; and based on a result of the analysis of the electrocardiogram in each of the analysis zones, execute determination whether electric shock on the patient is necessary or not, and calculate reliability of the determination; and a cardiopulmonary resuscitation post-procedure instructing section which, after instruction of the end of the procedure based on cardiopulmonary resuscitation, based on a combination of the determination and the reliability, is configured to instruct the operator on a procedure to be performed after the end of the procedure based on cardiopulmonary resuscitation.

The electrocardiogram analyzing section may be configured to detect whether or not a first waveform indicating that the electric shock is necessary or a second waveform indicating that the electric shock is not necessary is contained in the electrocardiogram in each of the analysis zones, and based on a number of detections of the first waveform or the second waveform, the electrocardiogram analyzing section may be configured to execute the determination whether the electric shock on the patient is necessary or not, and calculate the reliability of the determination.

The electrocardiogram analyzing section may be configured to classify a life-saving procedure state of the patient in each of the analysis zones, and based on the classified life-saving procedure state of the patient in each of the analysis zones, and the result of the analysis of the electrocardiogram in each of the analysis zones, the electrocardiogram analyzing section may be configured to execute the determination whether the electric shock on the patient is necessary or not, and calculate the reliability of the determination.

BRIEF DESCRIPTION OF THE DRAWINGS

FIG. 5A is a view in the case where chest compression is not performed, and FIG. 5B is a view in the case where chest compression is performed.

FIG. 6A is a view in the case where chest compression is not performed, and FIG. 6B is a view in the case where chest compression is performed.

FIG. 7 is a table showing the number of determinations that application of defibrillation is necessary, and that of determinations that application is not necessary, in a classification of an analysis zone.

DETAILED DESCRIPTION OF EXEMPLARY EMBODIMENTS

Hereinafter, an example of an embodiment of the defibrillator with a function of analyzing an electrocardiogram according to the presently disclosed subject matter will be described with reference to the drawings.

First Embodiment

Figure 1:
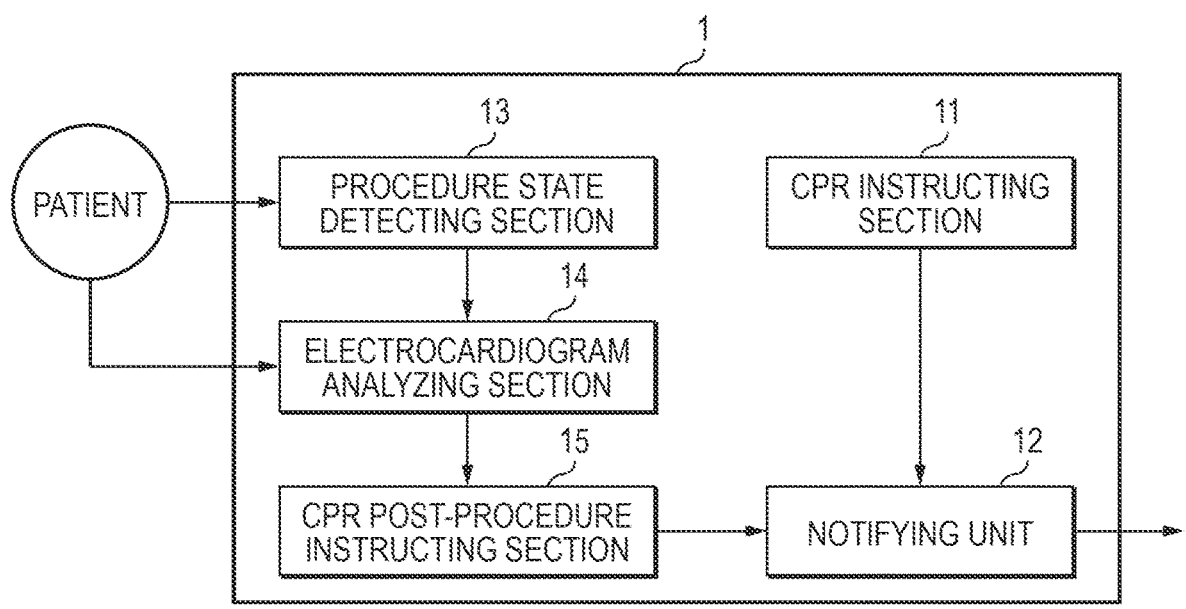
FIG. 1 is a block diagram showing an example of the function and configuration of the defibrillator with a function of analyzing an electrocardiogram according to the presently disclosed subject matter.

FIG. 1 shows the configuration of a defibrillator 1 with a function of analyzing an electrocardiogram. The defibrillator 1 with a function of analyzing an electrocardiogram has functions of analyzing an electrocardiogram of the subject (patient) during a CPR period, determining whether a fatal arrhythmia such as ventricular fibrillation or pulseless ventricular tachycardia occurs or not, and, based on a result of the determination, determining whether electric shock is to be performed or not.

As shown in FIG. 1, the defibrillator 1 with a function of analyzing an electrocardiogram includes: a cardiopulmonary resuscitation instructing section (hereinafter, referred to as CPR instructing section) 11 which instructs on the start and end of a procedure based on cardiopulmonary resuscitation (CPR); a notifying unit 12 configured by a speaker or the like; a procedure state detecting section 13 which detects whether a life-saving procedure based on CPR is performed or not; an electrocardiogram analyzing section 14 which comprehensively analyzes the procedure state of the patient and an electrocardiogram; and a cardiopulmonary resuscitation post-procedure instructing section (hereinafter, referred to as CPR post-procedure instructing section) 15 which instructs on the contents of a procedure that is to be performed on the patient after the end of CPR.

The defibrillator 1 of the embodiment is an automated external defibrillator (hereinafter, often abbreviated as AED) which can be used by an ordinary person. When the AED 1 is to be used, the rescuer (operator) first attaches pads (electrodes) to a cardiac arrest patient, based on instructions from the AED 1, an electrocardiogram analysis is performed under the state where the rescuer separates from the patient, and CPR is performed for about 2 minutes in accordance with a result of the analysis. The CPR instructing section 11 has a function of instructing the rescuer timings of starting and ending the CPR. The instructions are notified to the rescuer via the notifying unit (a speaker or the like) 12.

The procedure state detecting section 13 detects the procedure state (life-saving procedure state) of the patient and the specific contents of the life-saving procedure which is performed on the patient. Specifically, the life-saving procedure may be chest compression, artificial ventilation, electric shock, an electrocardiogram analysis, and the like.

The electrocardiogram analyzing section 14 comprehensively analyzes the procedure state of the patient and the specific contents of the life-saving procedure, which are detected by the procedure state detecting section 13, and the electrocardiogram which is measured from the patient. Based on a result of the analysis, the electrocardiogram analyzing section determines whether electric shock on the patient is necessary or not, and calculates the reliability of the determination on whether electric shock is necessary or not.

Based on a combination of the determination on whether electric shock is necessary or not and the reliability of the determination, the CPR post-procedure instructing section 15, instructs the rescuer on the contents of the procedure that is to be performed on the patient after the end of CPR. The instructions are issued immediately after the end of CPR is notified via the notifying unit 12. For example, the CPR post-procedure instructing section 15 instructs to perform a procedure such as a continuation of the CPR, an implementation of electric shock, an implementation of an electrocardiogram analysis, a check of the pulse, or the like.

With respect to the contents of the subsequent procedure, in the case where the instructed procedure is an implementation of electric shock, the AED 1 performs electric shock in accordance with the instructions. In the case of an implementation of an electrocardiogram analysis, the operator is notified to separate from the patient, and then an electrocardiogram analysis is automatically started. In the case of a check of the pulse, the pulse is checked in accordance with the instructions.

Next, the flow of the whole flowchart of an analysis of an electrocardiogram will be described with reference to FIG. 2. When the power supply of the AED 1 is first turned ON, the operation sequence of the life-saving procedure by the AED 1 is acoustically output from the notifying unit 12. In accordance with the audio instructions, the rescuer attaches the pads (electrodes) to predetermined positions of the patient, and starts CPR.

At the timing when the rescuer is instructed to perform CPR, in accordance with the instructions for starting CPR by the CPR instructing section 11 of the AED 1, the electrocardiogram analyzing section 14 starts an electrocardiogram analysis during the CPR period. During a period when CPR is performed (for example, about 2 minutes), i.e., until the CPR instructing section 11 issues instructions for ending the CPR, the electrocardiogram analysis is continuously performed in parallel with the CPR (step S101).

Processes (an analysis zone dividing step, a procedure state classifying step, an electrocardiogram analyzing step, and a determination calculating step) of the electrocardiogram analysis in step S101 will be described in detail later. The result of the electrocardiogram analysis in step S101 includes a result of the determination on whether electric shock on the patient is necessary or not (whether application of defibrillation is necessary, or the application is not necessary), and also a result of calculation of the reliability of the determination.

The start and end of the electrocardiogram analysis are not required to be notified to the rescuer, and the analysis operation is requested to be performed in the background. Namely, the rescuer is not necessary to perform a special operation on the AED 1. The procedure which is performed as CPR includes chest compression and artificial ventilation. For example, 5 sets of 30 chest compressions and 2 artificial ventilations are performed during two minutes of CPR.

When the CPR period ends, the contents of a procedure that is to be performed on the patient are then instructed based on a combination of the determination on whether application of defibrillation is necessary or the application is not necessary, and the reliability of the determination (steps S102 to S109: a procedure content instructing step).

When the CPR period ends, at first, the level of the reliability of the analysis result which is acquired in step S101, i.e., the result of the electrocardiogram analysis which is obtained in parallel with CPR is determined (step S102).

If, as a result of the determination of step S102, the reliability of the result of the electrocardiogram analysis is high, it is determined whether, in the result of the electrocardiogram analysis obtained during CPR, application of electric shock on the patient is necessary (application of defibrillation is necessary) or not (step S103).

If the result of the determination in step S103 is that application of defibrillation is necessary, the AED 1 instructs the rescuer to perform application of electric shock (step S104). In this case, unlike a related-art AED, instructions for the rescuer to separate from the patient, and an analysis of the electrocardiogram are not conducted. Therefore, the interruption time of chest compression which elapses until application of electric shock can be shortened by the time period required for these operations. The case where, in step S103, the determination result is that application of defibrillation is necessary means that the sensitivity indicating the accuracy of the analysis in step S102 is high. The sensitivity is a probability that, when a patient on whom application of electric shock is necessary to be performed is analyzed, the AED 1 instructs the rescuer to apply electric shock.

When the AED 1 checks that electric shock is applied, the AED instructs the rescuer to continue CPR (step S109), and the process returns to step S101.

By contrast, if it is determined in step S103 that application of defibrillation is not necessary, the AED 1 does not instruct the rescuer to perform an electrocardiogram analysis, but instructs to continue CPR (step S109), and the process returns to step S101. In this case, the AED 1 does not instruct the rescuer to separate from the patient, and therefore continuous chest compression is enabled. The determination result in step S103 that application of defibrillation is not necessary means that the specificity indicating the analysis accuracy in step S102 is high. The specificity is a probability that, when a patient on whom application of electric shock is not necessary to be performed is analyzed, the AED 1 shows the rescuer that electric shock is not necessary to be performed on the patient.

As described above, in the case where the reliability of the result of the analysis during CPR is high, the interruption time of chest compression can be shortened.

By contrast, if it is determined in step S102 that the reliability of the result of the electrocardiogram analysis is low, procedures (steps S105 to S109) which are the same as those in a related-art AED are performed. Namely, the rescuer is instructed to, in order to perform an electrocardiogram analysis, separate from the patient (step S105), and an electrocardiogram analysis in interruption of chest compression is performed (step S106). In the case where the reliability of the result of an electrocardiogram analysis is low, the analysis which has been employed in a related-art AED, and which involves interruption of chest compression is incorporated, whereby the accuracy of the analysis result indicated by the AED 1 can be maintained high.

Then, if the result of the analysis in step S106 shows that application of defibrillation is necessary (YES in step S107), the AED 1 instructs the rescuer to perform electric shock (step S108). After the AED checks that electric shock is applied, the AED instructs the rescuer to continue CPR (step S109), and the process returns to step S101.

If the result of the analysis in step S106 shows that application of defibrillation is not necessary (NO in step S107), the AED 1 instructs the rescuer to continue CPR (step S109), and the process returns to step S101. In this case, a procedure of "A check of the pulse of the patient is performed/not performed." may be added. When "not performed" is set, the contents of the above-described procedures are performed, and, when "performed" is set, a check of the pulse of the patient is instructed before a continuation of CPR is instructed in step S109.

Figure 2:
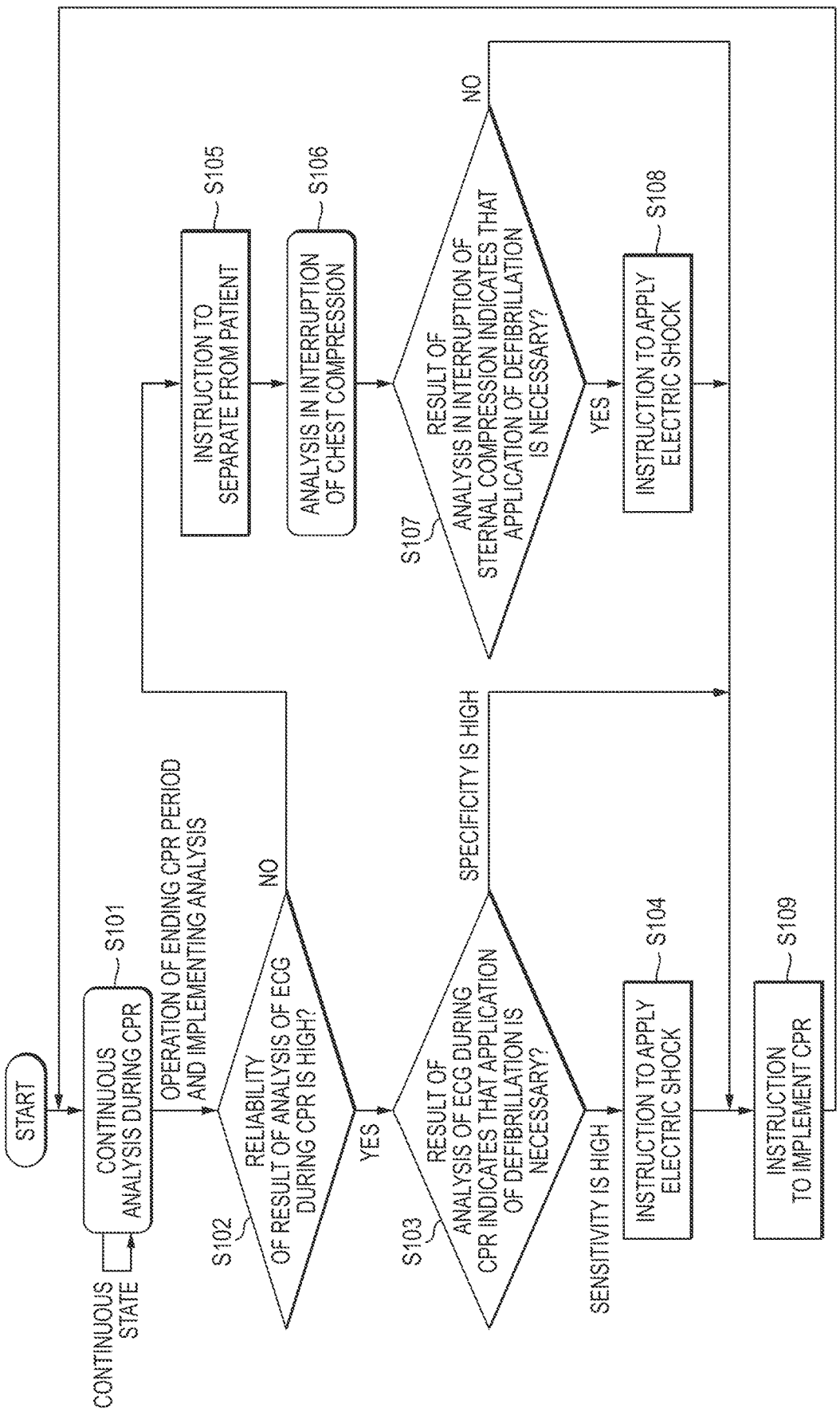
FIG. 2 is a flowchart showing an electrocardiogram analysis in the defibrillator with a function of analyzing an electrocardiogram according to the presently disclosed subject matter.

In the electrocardiogram analysis flowchart shown in FIG. 2, the CPR is analyzed immediately after the power supply of the AED 1 is turned ON. Alternatively, a mode may be employed where the processes of S105 to S109 are first performed, and then the CPR is analyzed or the process of S101 is performed. Next, the processes (the analysis zone dividing step, the procedure state classifying step, the electrocardiogram analyzing step, and the determination calculating step) of the electrocardiogram analysis in step S101 will be described in detail with reference to FIG. 3A to FIG. 6B.

Figure 3A:
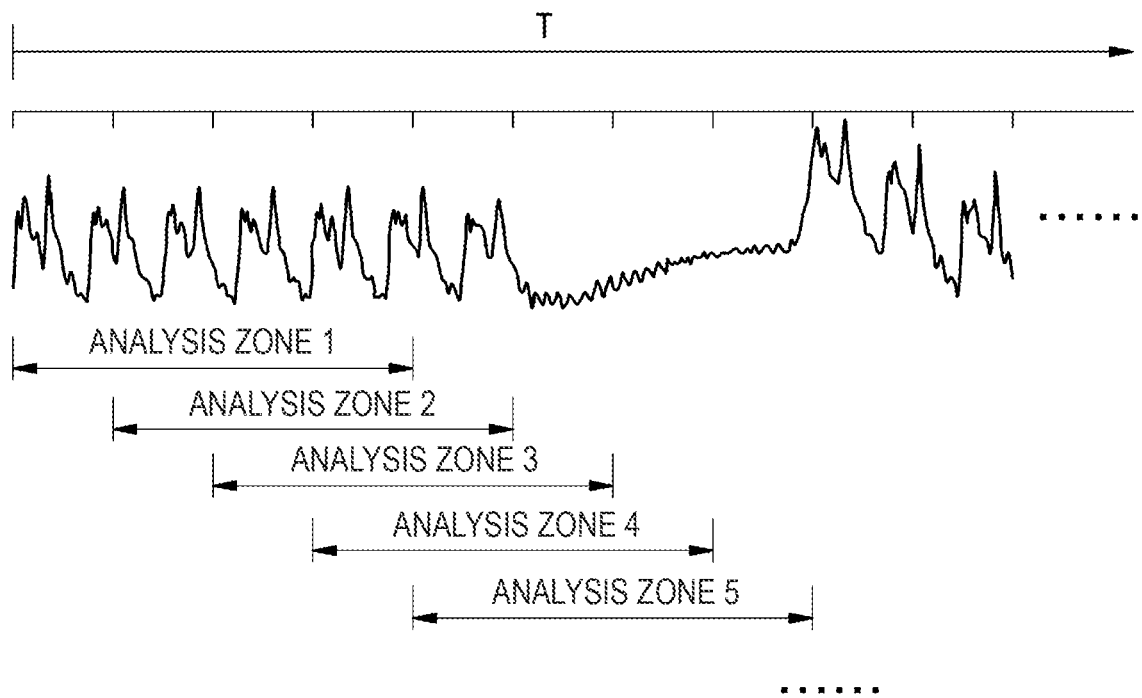
FIGS. 3A and 3B are views respectively showing modes in which an electrocardiogram measured during a CPR period is divided into a plurality of analysis zones.

The electrocardiogram analysis during CPR is performed while the electrocardiogram measured during the CPR period which is to be analyzed is divided into a plurality of zones (the analysis zone dividing step). Specifically, the analysis zone division may be performed by dividing the CPR period T into analysis zones (analysis zones 1, 2, 3, so as to partly overlap as shown in FIG. 3A. For example, analyses zones (analysis zones 1, 2, 3, . . . ) for a waveform of four seconds are performed while shifting the zones in steps of one second, and a result of an electrocardiogram analysis for 30 to 60 seconds is acquired.

Figure 3B:
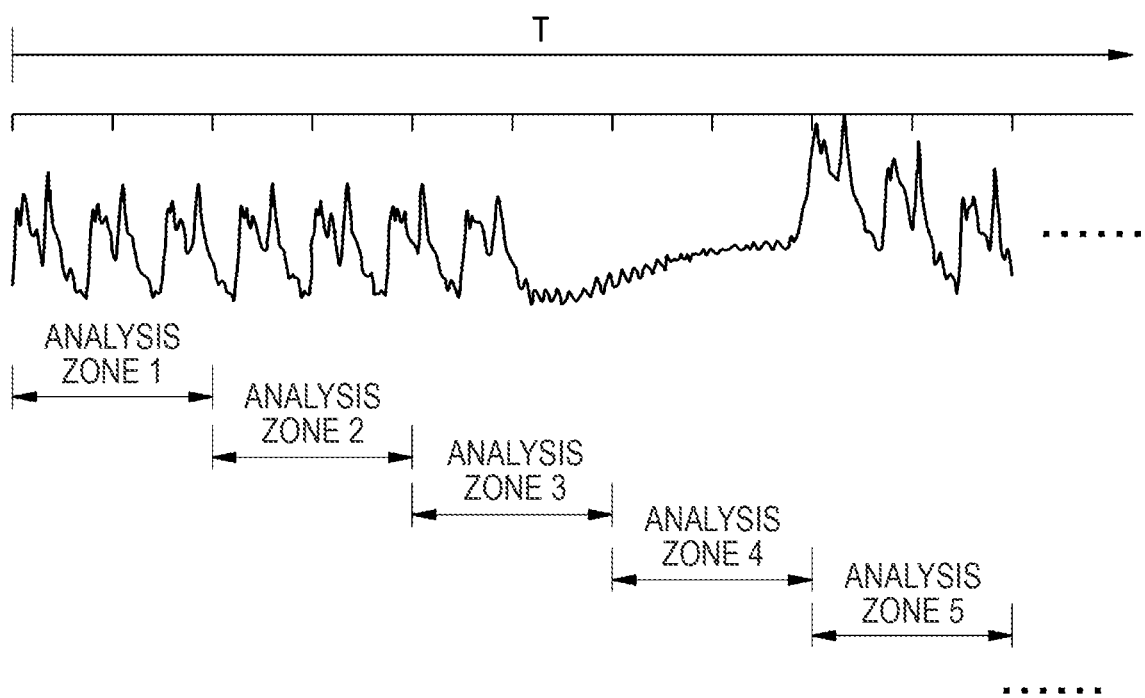

Alternatively, the analysis zone division may be performed so that analysis zones (analysis zones 1, 2, 3, . . . ) do not overlap with each other as shown in FIG. 3B. The division into the analysis zones is performed in the manner that, as shown in FIGS. 3A and 3B, the zones are continuous so as not to form a non-analysis zone between adjacent analysis zones. Then, results of analyses in the zones are integrated to make a final determination.

The procedure state (chest compression, artificial ventilation, or the like) which is applied to the patient during CPR is determined from an electrocardiogram measured during the CPR period. The determination of the procedure state is performed in each of the divided analysis zones of the electrocardiogram (the procedure state classifying step). The procedure state is determined based on the noise components of to-be-analyzed electrodes which contaminate the electrocardiogram, and classification into the following states is determined.

In the case where, from beginning to end of an analysis zone, an electrocardiogram is contaminated with noises (artifact), and it is determined that a procedure is performed on the patient, for example, the analysis zone is classified as "During procedure". In the case where, from beginning to end of an analysis zone, an electrocardiogram is not contaminated with noises, and it is determined that a procedure is not performed on the patient, the analysis zone is classified as "During interruption of procedure". In the case where, in a middle of an analysis zone, an electrocardiogram is contaminated or does not become contaminated with noises, and it is determined that application of procedure on the patient is started from the middle or ended (interrupted) in the middle, the analysis zone is classified as "Mixture".

Chest compression which is one of procedure states to be performed on the patient will be detected in the following manner.

Figure 4A:
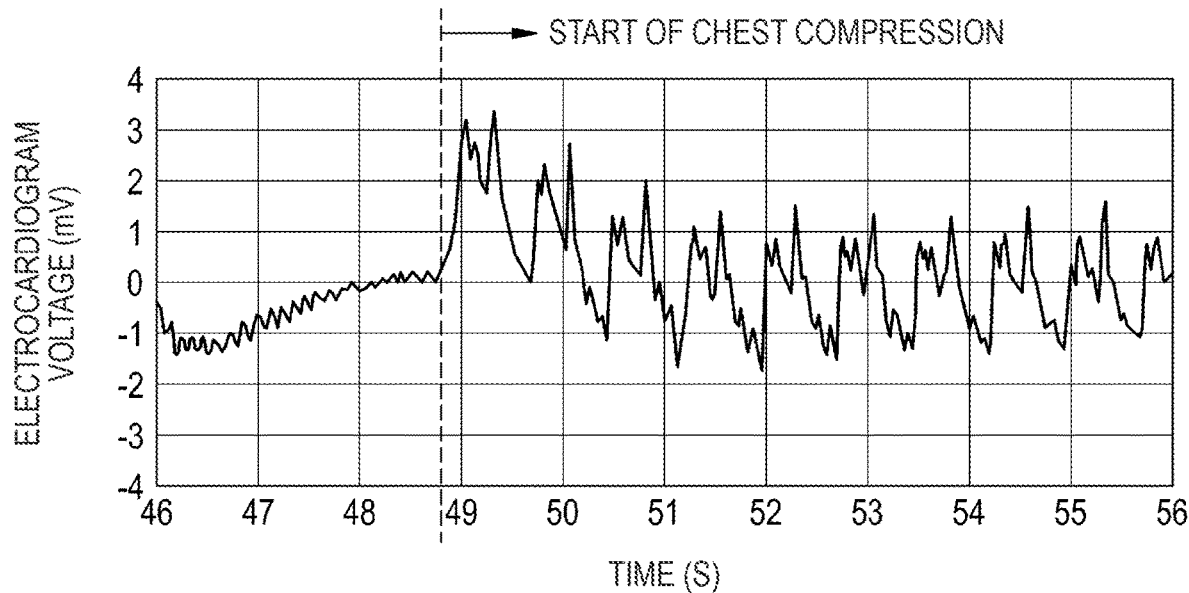
FIG. 4A is a view showing changes in an electrocardiogram at the time of starting chest compression.
Figure 4B:
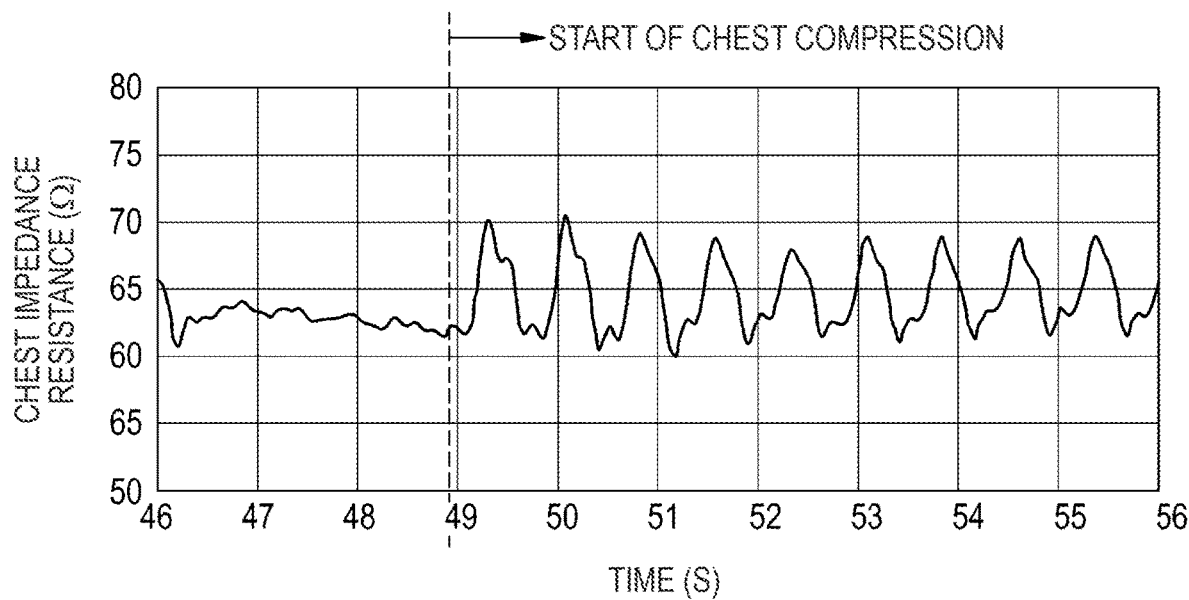
FIG. 4B is a view showing changes in thoracic impedance at the time of starting chest compression.

When chest compression is started, a change of the shape of an electrocardiogram is caused to appear by contamination of noise components as shown in FIG. 4A, and a change of the value of the thoracic impedance between the to-be-analyzed to electrodes is caused to appear as shown in FIG. 4B. When the chest compression is interrupted, changes opposite to the above appear. Therefore, the change of the electrocardiogram waveform, and that of the thoracic impedance are measured, and results of the measurements are integrated, thereby enabling detection on whether chest compression is performed or not.

When, for example, it is measured whether a portion where the amplitude largely changes in the electrocardiogram waveform of each divided analysis zone (see FIGS. 3A and 3B) exists or not, or it is measured whether an electrocardiogram waveform having a large amplitude exists periodically (in the intervals when chest compression is repeated) or not, chest compression can be detected. When, for example, it is measured whether a portion where the thoracic impedance is largely changed exists or not, or it is measured whether the change appears periodically (in the intervals when chest compression is repeated) or not, moreover, chest compression can be detected.

In each analysis zone, when it is measured whether a periodic electrocardiogram waveform having a large amplitude is continued from beginning to end of the zone or not, or when it is measured whether a periodic thoracic impedance having a large value is continued from beginning to end of the zone or not, the zone can be classified as "During procedure" of chest compression. Similarly, when it is measured that existence is started from a middle of a zone, or when it is measured that existence is ended in a middle of a zone, the zone can be classified as "Mixture" of chest compression.

Figure 5A:
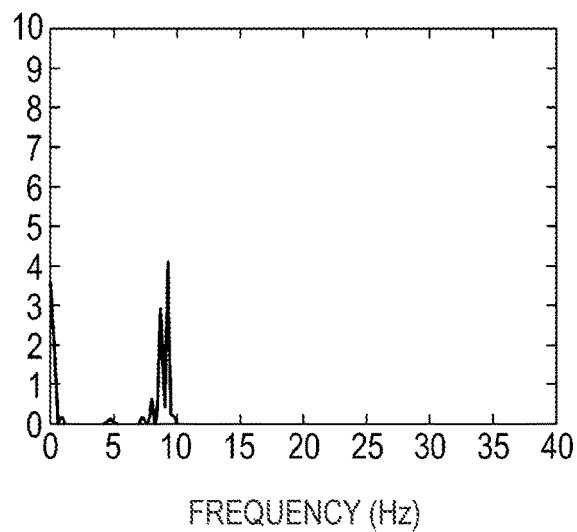
FIGS. 5A and 5B are views each of which shows a result of a frequency analysis of an electrocardiogram.
Figure 5B:
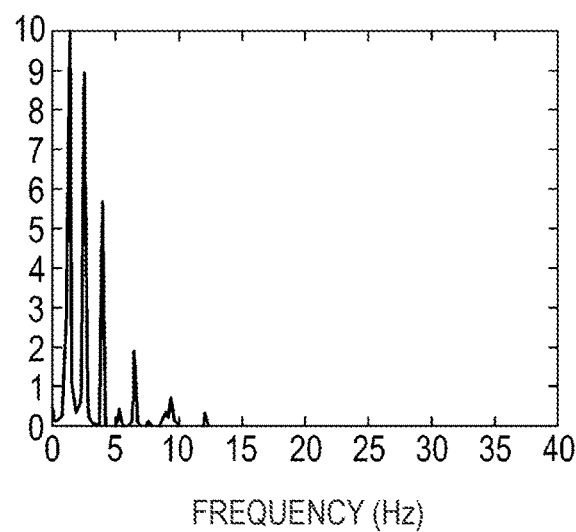

When chest compression is performed, a change appears also in results of frequency analyses of an electrocardiogram waveform and the thoracic impedance. Each of FIGS. 5A and 5B shows a result of a frequency analysis of an electrocardiogram, FIG. 5A is a view in the case where chest compression is not performed, and FIG. 5B is a view in the case where chest compression is performed. As shown in FIG. 5B, in the case where chest compression is preformed regularly (at a constant period), peaks appear in the vicinities of a frequency corresponding to the period of the chest compression, and its integer multiple frequencies in the result of the frequency analysis of an electrocardiogram.

Figure 6A:
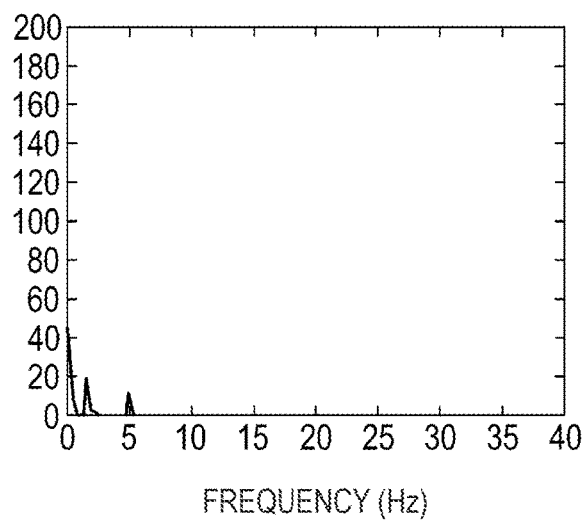
FIGS. 6A and 6B are views each of which shows a result of a frequency analysis of the thoracic impedance.
Figure 6B:
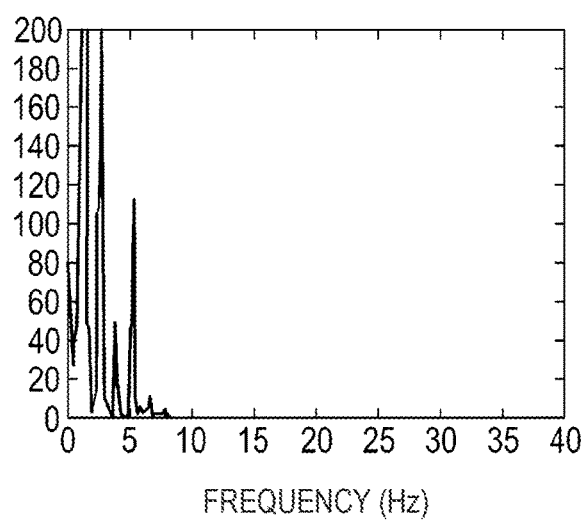

Each of FIGS. 6A and 6B shows a result of a frequency analysis of the thoracic impedance, FIG. 6A is a view in the case where chest compression is not performed, and FIG. 6B is a view in the case where chest compression is performed. As shown in FIG. 6B, in the case where chest compression is preformed regularly (at a constant period), peaks appear in the vicinities of a frequency corresponding to the period of the chest compression, and its integer multiple frequencies in the result of the frequency analysis of the thoracic impedance. When a frequency analysis of an electrocardiogram, and that of the thoracic impedance are performed, and peak frequencies of results of the analyses are measured, therefore, it is possible to detect whether chest compression is performed or not.

When the amplitude of a capnograph indicating the concentration of carbon dioxide in the expiratory, or a signal acquired from electrodes attached to the rescuer who performs chest compression is measured, alternatively, it is possible to detect whether chest compression is being performed or not. The electrodes attached to the rescuer are electrodes which are attached respectively to, for example, the chest compression portion of the patient, and the hand (the portion which is in contact with the patient) of the rescuer. The implementation of chest compression may be determined based on conduction between the electrodes.

Artificial ventilation which is one of procedure states to be performed on the patient will be detected in the following manner.

When artificial ventilation is started, a change appears in a CO2 partial pressure curve. This change can be detected by measuring the respiratory condition of the patient by using the thoracic impedance method or a capnograph in which the concentration of carbon dioxide is measured. When the respiratory condition of the patient is measured, therefore, it is possible to detect whether artificial ventilation is being performed or not.

In each analysis zone, then, the analysis in a time domain, and that with a frequency domain are conducted to calculate various parameters indicating features (the electrocardiogram analyzing step).

As parameters which are obtained by analyzing a time domain, for example, the following (1) to (6) may be defined:

(1) Average peak-to-peak amplitude: each analysis zone of an electrocardiogram is divided into ten equal subzones, the potential difference between the maximum value (peak) and the minimum value (valley) during a period from the start of each subzone to the end is set as a peak-to-peak amplitude, and the average of 10 peak-to-peak amplitudes is defined as the average peak-to-peak amplitude;

(2) Longest flat portion: 10% of the average amplitude is as a threshold, a portion where the amplitude is continuously within the threshold for 0.2 seconds or longer is set as a flat portion, and the time period of the longest flat portion in the analysis zone of the electrocardiogram is defined as the longest flat portion is defined as the longest flat portion;

(3) Total flat portion: 10% of the average amplitude is as a threshold, a portion where the amplitude is continuously within the threshold for 0.2 seconds or longer is set as a flat portion, and the total time period of flat portions in the analysis zone of the electrocardiogram is defined as the total flat portion;

(4) Number of inflection points: the number of points (inflection points) where the potential change in the analysis zone of the electrocardiogram is switched from rising to falling or from falling to rising;

(5) Number of pulses: the number of independent waveforms in the analysis zone of the electrocardiogram, such as the QRS waveform; and (6) Average pulse width: an average value of widths of waveforms which are recognized as a pulse in the analysis zone of the electrocardiogram.

As parameters which are obtained by analyzing a frequency domain, for example, the following (1) to (5) may be defined:

(1) Maximum peak frequency: the frequency in which the amplitude is largest in the range of 1 to 30 Hz;

(2) Spectrum area ratio A: the value which is obtained by dividing a spectrum area of 1 to 2 Hz by a spectrum area of 1 to 30 Hz;

(3) Spectrum area ratio B: the value which is obtained by dividing a spectrum area of 2 to 12 Hz by the spectrum area of 1 to 30 Hz;

(4) Spectrum area ratio C: the value which is obtained by diving a spectrum area of 12 to 30 Hz by the spectrum area of 1 to 30 Hz; and (5) Spectrum peak number: the number of peaks which are between 1 to 30 Hz.

Then, electrocardiogram waveforms in the analysis zones are classified into the following (1) to (3), and the classification and pattern of the classification to which each analysis zone belongs are determined based on the parameters.

(1) During interruption of procedure: Defibrillation-necessary pattern 1, Defibrillation-necessary pattern 2, Defibrillation-necessary pattern 3, Non-applied pattern 1, Non-applied pattern 2, Non-applied pattern 3, (2) Mixture: Defibrillation-necessary pattern 1, Defibrillation-necessary pattern 2, Defibrillation-necessary pattern 3, Non-applied pattern 1, Non-applied pattern 2, Non-applied pattern 3, . . . .

(3) During procedure: Defibrillation-necessary pattern 1, Defibrillation-necessary pattern 2, Defibrillation-necessary pattern 3, . . . , Non-applied pattern 1, Non-applied pattern 2, Non-applied pattern 3, . . . .

In the case of (1) During interruption of procedure, for example, following Non-applied patterns 1 to 5 can be defined:

Non-applied pattern 1: the average amplitude is lower than 0.1 mV;

Non-applied pattern 2: the longest flat portion is 2 seconds or longer;

Non-applied pattern 3: the number of inflection points is smaller than 150/minute;

Non-applied pattern 4: the maximum peak frequency is 15 Hz or higher; and

Non-applied pattern 5: the average amplitude is 0.1 mV or higher or lower than 0.2 mV, the number of pulses is smaller than 180/minute, the maximum peak frequency is lower than 5 Hz, and the spectrum area ratio C is 30% or more.

A determination result that the analysis zone is during interruption of procedure indicates that the accuracy of the analysis result is high. Another determination result that the analysis zone is mixture or during procedure indicates that the accuracy of the analysis result is low. While weighting is conducted with setting the level of the accuracy as a coefficient, therefore, the total number of defibrillation-necessary cases, and that of non-applied cases are calculated.

At this time, the numbers of cases which are in during interruption of procedure, and which correspond to defibrillation-necessary patterns are defined as $Nsa(1)$, $Nsa(2)$, $Nsa(3)$, . . . , $Nsa(k)$, and the weight coefficients are defined as $\alpha s(1)$, $\alpha s(2)$, $\alpha s(3)$, . . . , $\alpha s(k)$. The numbers of cases which are during interruption of procedure, and which correspond to non-applied patterns are defined as $Nna(1)$, $Nna(2)$, $Nna(3)$, . . . , $Nna(k)$, and the weight coefficients are defined as $\alpha n(1)$, $\alpha n(2)$, $\alpha n(3)$, . . . , $\alpha n(k)$.

Moreover, the numbers of cases which are in mixture, and which correspond to defibrillation-necessary patterns are defined as $Nsb(1)$, $Nsb(2)$, $Nsb(3)$, . . . , $Nsb(k)$, and the weight coefficients are defined as $\beta s(1)$, $\beta s(2)$, $\beta s(3)$, . . . , $\beta s(k)$. The numbers of cases which correspond to non-applied patterns are defined as $Nnb(1)$, $Nnb(2)$, $Nnb(3)$, . . . , $Nnb(k)$, and the weight coefficients are defined as $\beta n(1)$, $\beta n(2)$, $\beta n(3)$, . . . , $\beta n(k)$.

Furthermore, the numbers of cases which are during procedure, and which correspond to defibrillation-necessary patterns are defined as $Nsc(1)$, $Nsc(2)$, $Nsc(3)$, . . . , $Nsc(k)$, and the weight coefficients are defined as $\gamma s(1)$, $\gamma s(2)$, $\gamma s(3)$, . . . , $\gamma s(k)$. The numbers of cases which correspond to non-applied patterns are defined as $Nnc(1)$, $Nnc(2)$, $Nnc(3)$, . . . , $Nnc(k)$, and the weight coefficients are defined as $\gamma n(1)$, $\gamma n(2)$, $\gamma n(3)$, . . . , $\gamma n(k)$.

From the number of cases of patterns, and the weight coefficients, the total number of defibrillation-necessary cases in all weighted zones is expressed by the following expression.

$$Nsw = \Sigma\{\alpha_s(k) \times Nsa(k)\} + \Sigma\{\beta_s(k) \times Nsb(k)\} + \Sigma\{\gamma_s(k) \times Nsc(k)\}$$

From the number of cases of patterns, and the weight coefficients, the total number of non-applied cases in all weighted zones is expressed by the following expression.

$$Nsw = \Sigma\{\alpha_n(k) \times Nsa(k)\} + \Sigma\{\beta_n(k) \times Nsb(k)\} + \Sigma\{\gamma_n(k) \times Nsc(k)\}$$

If $Nsw \geq Nnw$, it is determined that application of defibrillation is necessary, and, if $Nsw < Nnw$, it is determined that application is not necessary (the determination calculating step).

Alternatively, the determination on whether application of defibrillation is necessary, or the application is not necessary may be performed in the following sequence.

In the classification of analysis zones, the number of determinations that application of defibrillation is necessary, and that of determinations that application is not necessary are set as shown in FIG. 7. The total number Ns of defibrillation-necessary cases in all the analysis zones is $Ns = i + j + k$, and the total number Nn of non-applied cases in all the analysis zones is $Nn = l + m + n$.

The case where the analysis zone is during interruption of procedure indicates that the accuracy of the analysis result is high, and that where the analysis zone is mixture or during procedure indicates that the accuracy of the analysis result is low.

While weighting is conducted with setting the level of the accuracy as a coefficient, therefore, the total number of defibrillation-necessary cases, and that of non-applied cases are calculated. When zones of during interruption of procedure, mixture, and during procedure are weighted by coefficients $\alpha$, $\beta$, and $\gamma$, respectively, the total number Nsw of defibrillation-necessary cases in all weighted analysis zones is $Nsw = \alpha i + \beta j + \gamma k$, and the total number Nnw of non-applied cases in all the weighted analysis zones is $Nnw = \alpha l + \beta m + \gamma n$.

If $Nsw \geq Nnw$, it is determined that application of defibrillation is necessary, and, if $Nsw < Nnw$, it is determined that application is not necessary.

Here, $\alpha$, $\beta$, and $\gamma$ may not be fixed values, and may be variable values. In the case of variable values, the values are fixed by the method which will be described below.

Considering the ease of an erroneous determination in the pattern classification in each procedure classification, a plurality of values of corresponding coefficients are first determined as $\alpha 1$, $\alpha 2$, $\alpha 3$, ($\alpha 1 > \alpha 2 > \alpha 3 > $ . . . ), $\beta 1$, $\beta 2$, $\beta 3$, . . . ($\beta 1 > \beta 2 > \beta 3 >$ . . . ), and $\gamma 1$, $\gamma 2$, $\gamma 3$, . . . ($\gamma 1 > \gamma 2 > \gamma 3 >$ . . . ). For example, the determination is made as follows: Defibrillation-necessary patterns 1 to 10 and Non-applied patterns 1 to 10 during interruption of procedure correspond to the coefficient $\alpha 1$; Defibrillation-necessary patterns 11 to 20 and Non-applied patterns 11 to 20 during interruption of procedure correspond to the coefficient $\alpha 2$; and Defibrillation-necessary patterns 21 to 30 and Non-applied patterns 21 to 30 during interruption of procedure correspond to the coefficient $\alpha 3$.

Next, coefficients corresponding to the pattern which is calculated at most in an analysis zone that is classified as during interruption of procedure (the pattern which is mostly included in i and l), that which is calculated at most in an analysis zone that is classified as mixture (the pattern which is mostly included in j and m), and that which is calculated at most in an analysis zone that is classified as during procedure (the pattern which is mostly included in k and n) are set as $\alpha$, $\beta$, and $\gamma$, respectively.

The electrocardiogram analysis during CPR is continuously implemented in a plurality of analysis zones. In order to fix a result of the analysis of whether electric shock is necessary or not, analysis results in analysis zones of a given number or more are required so as to enhance the accuracy of the analysis result. In the case where CPR is performed, there is a possibility that the patient's condition is changed, and, in order to make a determination on whether electric shock is necessary or not, it is preferable that most recent data are used as far as possible as the analysis target. In the case where analysis zones the number of which is equal to or larger than a given number that is necessary in continuous analyses, therefore, the result of the oldest analysis zone may be sequentially omitted from the analysis target.

Next, the calculation of the reliability of the above-described determination on whether electric shock is necessary or not will be described.

The reliability is comprehensively calculated while using a plurality of items as factors (the determination calculating step). In the case where the procedure state of the analysis zone is classified as during interruption of procedure, for example, it is shown that an electrocardiogram which is not contaminated with noises due to implementation of chest compression during CPR can be already analyzed, and the result of the analysis can be already used in determination on whether electric shock is necessary or not. Therefore, this is a factor of causing the reliability to be calculated to be high.

In the case where the procedure state of the analysis zone is classified as during procedure, and analysis patterns of the electrocardiogram coincide with each other in a plurality of analysis zones, it is shown that, during CPR, there is no change in the electrocardiogram of the patient (a change such as that in which ventricular fibrillation is developed to cardiac arrest does not occur), the period and strength of chest compression are constant (noises caused to contaminate by the procedure are constant), and a filtering process on noises effectively functions. Therefore, this is a factor of causing the reliability to be calculated to be high.

In the case where a waveform which is flat for a given time period or longer (for example, 4 seconds or longer) is recorded in an analysis zone, there is a high possibility that noises due to chest compression are not produced during the time period, and a potential change due to the heart is not caused, or the patient falls into cardiac asystole that is one of electrocardiograms in which electric shock is not necessary. As described above, in the case where a characteristic waveform is recorded, this is a factor of causing the reliability to be calculated to be high, irrespective of the classification of the procedure state.

By contrast, in the case where the total number of analysis zones does not exceed the given number, this is a factor of causing the reliability to be calculated to be low. In a current rescue protocol, the time period of CPR is set to about two minutes. The time period is enough long to perform continuous analyses during CPR, and the total number of analysis zones can sufficiently exceed the given number. On the other hand, in a semi-automated external defibrillator which is to be used by a qualified person such as a paramedic, the rescuer can determine the timing of an analysis, and hence there is a possibility that the CPR period is shortened. In this case, therefore, the total number of analysis zones may not exceed the given number, and this may be a factor of causing the reliability to be low.

Although the AED 1 has a measurement range of an amplitude which is sufficient to measure an electrocardiogram during CPR, in the case where, in any analysis zone, the amplitude of an electrocardiogram exceeds the range which can be measured by the AED 1, a factor of causing the reliability to be calculated to be low is set. In this case, the analysis zone which exceeds the measurable range may be omitted from the determination target, but a state where the total number does not exceed the given number can be caused by the omission of the analysis zone may occur. For the same reason as described above, this is a factor of causing the reliability to be calculated to be low.

In the case where, in any analysis zone, it is detected that the electrodes for measuring an electrocardiogram are detached, this is a factor of causing the reliability to be calculated to be low. In this case, the analysis zone in which the detachment of the electrodes is detected may be omitted from the determination target. Similarly with the above case, because of the relationship of the total number of analysis zones, however, this is a factor of causing the reliability to be calculated to be low. As described above, for example, the reliability is comprehensively calculated while using the plurality of items as factors.

FIGS. 8A to 8D diagrammatically show a manner of shortening the CPR interruption time in the case where the reliability of a result of an electrocardiogram analysis performed during CPR is high.

Figure 8A:
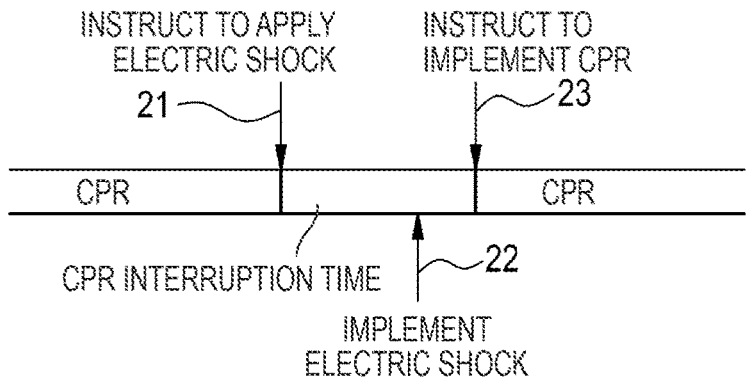
FIGS. 8A and 8B are views showing a comparison of CPR interruption times in the case of an electrocardiogram in which electric shock is necessary.
Figure 8B:
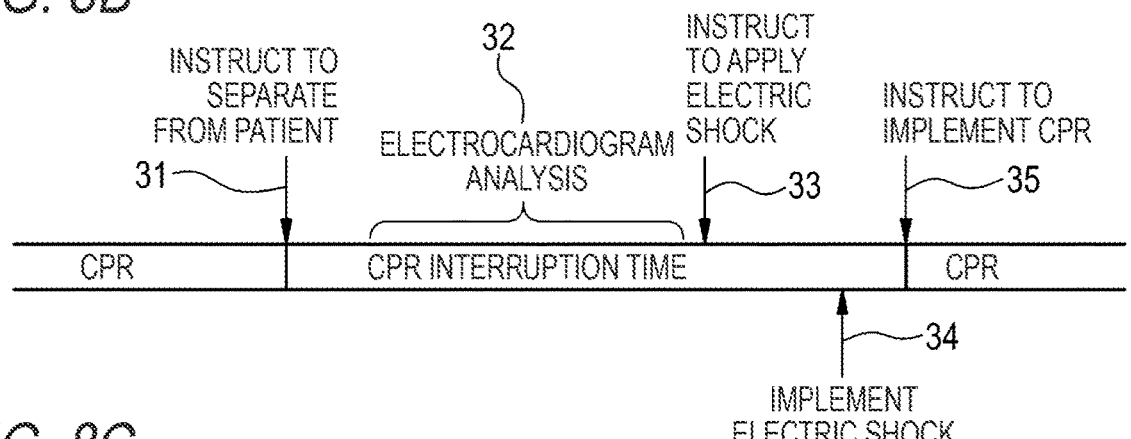

FIGS. 8A and 8B are views showing a comparison of CPR interruption times in the case of an electrocardiogram in which it is determined that electric shock is necessary. In the case of a comparison example (the operation of a related-art AED) shown in FIG. 8B, the AED instructs the rescuer to separate from the patient, at the timing of the arrow 31 when CPR ends. Thereafter, an electrocardiogram analysis 32 is implemented, and instructions for electric shock are performed at the timing of the arrow 33. The rescuer receives the instructions for electric shock, and then presses down a shock button to perform electric shock at the timing of the arrow 34. After electric shock is performed, the AED instructs on implementation of CPR at the timing of the arrow 35.

By contrast, in the case of the AED 1 shown in FIG. 8A, it is fixed that electric shock is necessary, at the timing of the arrow 21 when CPR ends, and therefore instructions for electric shock is immediately issued. The rescuer receives the instructions for electric shock, and then presses down the shock button to perform electric shock at the timing of the arrow 22. After electric shock is performed, the AED 1 instructs on implementation of CPR at the timing of the arrow 23.

As described above, in the case where electric shock is necessary, the time period which is necessary in a related-art AED, and which elapses from the issuance of instructions for separation from the patient until the end of the electrocardiogram analysis is not necessary in the AED 1. Therefore, the interruption time of chest compression can be correspondingly shortened.

Figure 8C:
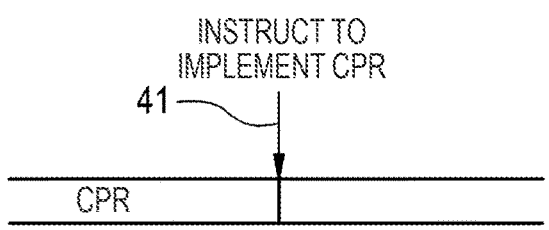
FIGS. 8C and 8D are views showing a comparison of CPR interruption times in the case of an electrocardiogram in which electric shock is not necessary.
Figure 8D:
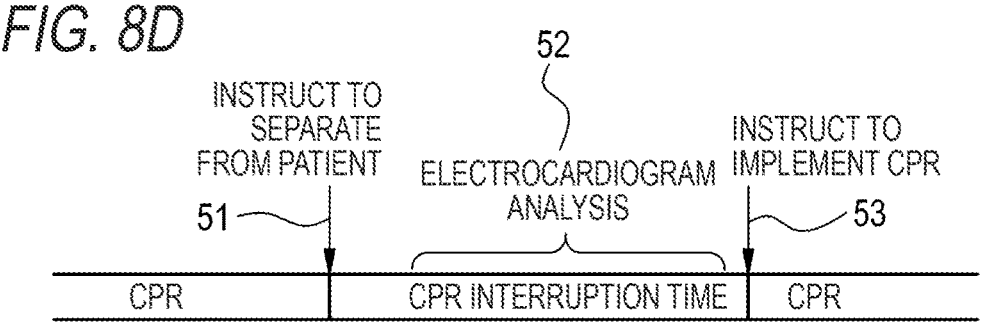

FIGS. 8C and 8D are views showing a comparison of CPR interruption times in the case of an electrocardiogram in which electric shock is not necessary. In the case of a comparison example (the operation of a related-art AED) shown in FIG. 8D, the AED instructs the rescuer to separate from the patient, at the timing of the arrow 51 when CPR ends. Thereafter, an electrocardiogram analysis 52 is implemented, and the AED instructs the rescuer to perform CPR, at the timing of the arrow 53 when it is determined that electric shock is not necessary.

By contrast, in the case of the AED 1 shown in FIG. 8C, it is fixed that electric shock is not necessary at the timing of the arrow 41 when CPR ends, and therefore instructions for implementation of CPR is immediately issued.

As described above, also in the case where electric shock is not necessary, similarly with the above-described case where electric shock is necessary, the time period which elapses from the issuance of instructions for separation from the patient until the end of the electrocardiogram analysis is not necessary in the AED Therefore, the interruption time of chest compression can be correspondingly shortened.

Moreover, in the case where the reliability of the result of an electrocardiogram analysis is low, procedures (steps S105 to S109) which are similar to those in a related-art AED are performed. Namely, in the case where the reliability of the result of an electrocardiogram analysis is low, the analysis which has been employed in a related-art AED, and which involves interruption of chest compression is performed, whereby the accuracy of the analysis result can be maintained high.

(Modifications)

Figure 9:
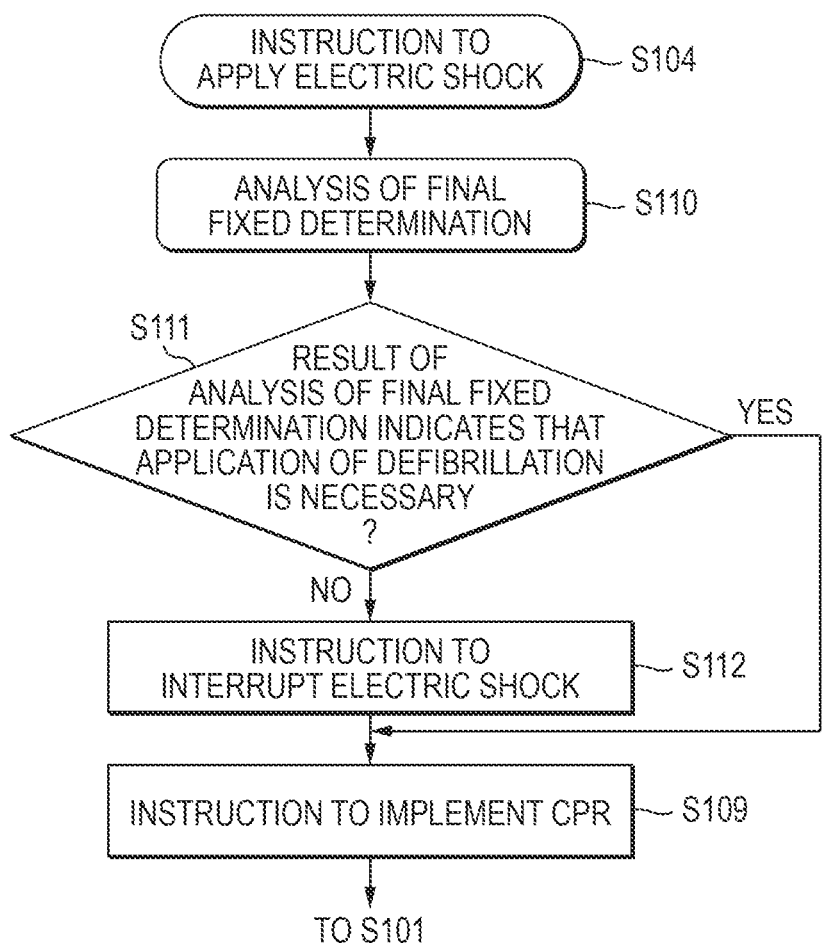
FIG. 9 is a flowchart in the case where an analysis of final fixed determination is added to FIG. 2.

FIG. 9 shows a flowchart in the case where an analysis process related to 'final fixed determination of electrocardiogram' is added to the flowchart of FIG. 2. As shown in the figure, processes of steps S110 to S112 are added between steps S104 and S109 in the flowchart of FIG. 2.

After instructions for electric shock are issued in step S104, final fixed determination with respect to an electrocardiogram is analyzed (step S110). In the analysis, the situation where, when electric shock is to be performed, the rescuer always separates from the patient is used, or namely an electrocardiogram which is not contaminated with noises, and which is produced when the rescuer separates from the patient is to be measured. The analysis accuracy can be further improved by referring a result of an analysis of an electrocardiogram which is not contaminated with noises, in addition to the result of the analysis during CPR in step S101.

Preferably, the state where the rescuer separates from the patient is maintained until an analysis result of final fixed determination in step S110 is obtained. If required, therefore, it is preferred to deliver a message 'Charging' in succession to a message 'Shock advised. Do not touch patient.' which notifies implementation of electric shock, thereby setting a state where the rescuer separates from the patient and implementation of electric shock is waited.

Then, it is determined whether, in the analysis result of final fixed determination, application of defibrillation is necessary or not (step S111). If it is determined in step S111 that also the analysis result of final fixed determination shows that application of defibrillation is necessary, or if the contents of the procedure which is determined from the analysis result, and which is to be applied on the patient coincides in step S111 with the procedure contents (electric shock) instructed in the procedure content instructing step (step S103), instructions which are necessary for implementing electric shock, such as 'Press flashing button' may be given to the rescuer. After the implementation of electric shock is confirmed, the rescuer is instructed to continue CPR (step S109).

By contrast, if it is determined in step S111 that the analysis result of final fixed determination shows that application is not necessary, an abort of the application of electric shock is instructed to the rescuer by giving a message such as 'Heart rhythm changed. Shock cancelled.' (step S112). Then, continuation of CPR is instructed (step S109), and the process returns to step S101.

In this case, a procedure such as "After change of electrocardiogram, perform/not perform reanalysis" may be additionally disposed. When "Not perform" is set, the contents of the above-described procedures are performed, and, when "Performed" is set, a reanalysis is instructed to be performed, before a continuation of CPR is instructed in step S109, whereby the rescuer is allowed to implement an electrocardiogram analysis which is to be performed while separating from the patient.

During a period when the contents of a procedure in the procedure content instructing step (step S103) is instructed, namely, during a period when the rescuer who is to perform electric shock separates from the patient, an electrocardiogram which is not contaminated with noises is measured and analyzed (S110). If the contents of the procedure which is determined from the analysis result, and which is to be applied on the patient coincide with the procedure contents (electric shock) instructed in the procedure content instructing step, instructions for the procedure contents are continued. If not coincident, the procedure contents are changed (a final fixation determining step).

As described above, in the defibrillator 1 with a function of analyzing an electrocardiogram according to the embodiment, and the method of controlling it, in order to shorten the chest compression interruption time, an electrocardiogram is analyzed in the background, also during a period when CPR is performed. The electrocardiogram analysis is performed while a zone to be analyzed is divided into a plurality of subzones. In each analysis zone, it is determined whether or not a procedure such as chest compression or artificial ventilation is performed in addition to extraction of features of the electrocardiogram. From results of these processes, not only determination on whether electric shock is necessary or not, but also calculation of the reliability of the determination are performed.

If the reliability of the determination is high, instructions for realizing a shortening of the interruption time of chest compression may be given to the rescuer. In the case of an electrocardiogram in which electric shock is necessary, for example, the AED 1 issues instructions for performing electric shock, at the timing when CPR ends. Therefore, the interruption time of chest compression can be shortened.

If the reliability of the determination is low, instructions for realizing a shortening of the interruption time of chest compression is not given. In this case, as with a related-art AED, instructions for separating from the patient are given to the operator at the timing when CPR ends, and thereafter an electrocardiogram analysis are performed. In the case where the reliability of the analysis result of an electrocardiogram during CPR is low, namely, the analysis which has been employed in a related-art AED, and which involves interruption of chest compression is performed, whereby the accuracy of the analysis result can be maintained high.

Moreover, the CPR period is divided into a plurality of subzones, the classification of the procedure state and the electrocardiogram analysis are performed in each of the divided analysis zones of the electrocardiogram, and determination of the necessity of electric shock, and calculation of the reliability of the determination are conducted based on the classification and the analysis. Therefore, the accuracy of the electrocardiogram analysis during CPR can be enhanced.

Moreover, the procedure state is classified into during procedure, during interruption of procedure, and mixture. Therefore, the accuracy of the electrocardiogram analysis can be further improved, and the reliability of the determination of the necessity/unnecessity of electric shock can be enhanced, so that the interruption time of chest compression can be surely shortened.

Moreover, the determination of the procedure state is performed based on the thoracic impedance, the frequency characteristic of an electrocardiogram, the amplitude of the electrocardiogram, the amplitude of a capnograph, a signal acquired from the electrodes attached to the rescuer who performs the chest compression, or the like. Therefore, determination that is more correct is enabled, and the reliability of determination of the necessity/unnecessity of electric shock can be enhanced, so that the interruption time of chest compression can be surely shortened.

Moreover, the reliability of determination of the necessity/unnecessity of electric shock is calculated based on reliability determination information including: implementation of an analysis of an electrocardiogram during interruption of procedure; coincidence of results of electrocardiogram analyses during procedure; the amplitude range of the electrocardiogram; the period of chest compression; a result of a frequency analysis of the electrocardiogram during chest compression; or the like. Therefore, a more correct reliability can be calculated, and the interruption time of chest compression can be surely shortened.

In order to realize a shortening of the interruption time of chest compression, it is requested that a high accuracy be maintained at the timing when the defibrillator finally gives instructions for necessity of electric shock to the operator, and at the timing when instructions for continuation of CPR are issued. An electrocardiogram which is measured during when procedure contents are instructed is analyzed, and final procedure contents are changed by comparison with a result of the analysis. Therefore, a higher analysis accuracy can be maintained, and the interruption time of chest compression can be surely shortened.

In an electrocardiogram which is divided into a plurality of subzones, an electrocardiogram measured in the latest given time period and contained in the latest subzones of the plurality of subzones is set as the analysis target. Therefore, the condition of the patient can be obtained more correctly, and an adequate procedure can be applied, so that a shortening of the interruption time of chest compression can be surely realized. In the case where the total number of analysis zones exceeds a preset given number, old analysis data are sequentially discarded. Therefore, the condition of the patient can be obtained more correctly based on the latest analysis result, and an adequate procedure can be applied, so that a shortening of the interruption time of chest compression can be surely realized.

Defibrillators are classified into an automated external defibrillator (AED) which can be used by an ordinary person, and a semi-automated external defibrillator which is to be used by a medical person such as a paramedic. The embodiment has been described by exemplifying an automated external defibrillator (AED). In any of defibrillators, in order to perform electric shock, an electrocardiogram analysis by the defibrillator is necessary. The presently disclosed subject matter can be applied to both of the defibrillators.

Second Embodiment

Next, a second embodiment of the presently disclosed subject matter will be described. The second embodiment is different from the first embodiment in that the defibrillator 1 does not have the procedure state detecting section 13.

In the defibrillator 1 of the second embodiment, the electrocardiogram analyzing section 14 analyzes an electrocardiogram measured during the CPR period, while dividing the electrocardiogram into a plurality of zones. The electrocardiogram analyzing section 14 analyzes whether or not the electrocardiogram in each analysis zone contains a defibrillation-necessary waveform having a high degree of certainty (an example of a first waveform (first-type waveform) indicating that electric shock is necessary), and a non-applied waveform having a high degree of certainty (an example of a second waveform (second-type waveform) indicating that electric shock is not necessary). For example, the defibrillation-necessary waveform having a high degree of certainty is a VF (ventricular fibrillation) waveform which has the maximum peak of 5 Hz or higher, and which can be distinguished from the chest compression rate of 1.67 Hz, and the non-applied waveform having a high degree of certainty is a waveform in which a flat portion continues for 2 seconds or longer in 4 seconds. A flat waveform shows that potential changes due to the heart and chest compression do not exist.

While dividing and analyzing an electrocardiogram as described above, the electrocardiogram analyzing section 14 counts the numbers of detections of a defibrillation-necessary waveform having a high degree of certainty and a non-applied waveform having a high degree of certainty, during one CPR period (for example, 2 minutes). In the case where, during one CPR period, a defibrillation-necessary waveform having a high degree of certainty is counted two times, and a non-applied waveform having a high degree of certainty is counted zero time, for example, the electrocardiogram analyzing section 14 determines that electric shock is necessary and the reliability is high, and transmits the determination of the necessity/unnecessity of electric shock, and the reliability of the determination to the CPR post-procedure instructing section 15. The CPR post-procedure instructing section 15 issues instructions for implementing electric shock at the timing of the end of CPR, based on the information indicating that electric shock is necessary and the reliability is high. Therefore, the interruption time of chest compression can be shortened.

In the case where, during one CPR period, a defibrillation-necessary waveform having a high degree of certainty is counted zero time, and a non-applied waveform having a high degree of certainty is counted two times, for example, the electrocardiogram analyzing section 14 determines that electric shock is not necessary and the reliability is high, and transmits the determination of the necessity/unnecessity of electric shock, and the reliability of the determination to the CPR post-procedure instructing section 15. The CPR post-procedure instructing section 15 issues instructions for continuously implementing electric shock at the timing of the end of CPR, based on the information indicating that electric shock is not necessary and the reliability is high. Therefore, the interruption time of chest compression can be shortened.

In the case where, during one CPR period, a defibrillation-necessary waveform having a high degree of certainty is counted one time, and a non-applied waveform having a high degree of certainty is counted zero time, for example, the electrocardiogram analyzing section 14 determines that electric shock is necessary and the reliability is low, and transmits the determination of the necessity/unnecessity of electric shock, and the reliability of the determination to the CPR post-procedure instructing section 15. The CPR post-procedure instructing section 15 issues instructions at the timing of the end of CPR for, after giving instructions for separating from the patient to the operator, implementing electric shock based on the information indicating that electric shock is necessary and the reliability is low. In the case where the reliability of the analysis result during CPR is low, therefore, the analysis which has been employed in a related-art AED, and which involves interruption of chest compression is performed, whereby the accuracy of the analysis result can be maintained high.

According to an aspect of the presently disclosed subject matter, based on a result of an electrocardiogram analysis during CPR, adequate instructions are provided to the rescuer (operator) with an accuracy which is equivalent to that of an analysis that is performed under noise-free conditions, and the interruption time of chest compression can be shortened.

What is claimed is:

1. A method of controlling a defibrillator with a function of analyzing an electrocardiogram, during a first procedure related to cardiopulmonary resuscitation, the method comprising:
dividing an electrocardiogram of a patient into a plurality of analysis zones;
executing analysis of the electrocardiogram in each of the divided analysis zones to obtain, as analysis results, only one result of the analysis in each of the divided analysis zones of the electrocardiogram obtained during the first procedure;
based on the analysis results:
executing a determination of whether electric shock on the patient is necessary or not; and
calculating reliability of the determination;
determining a level of the reliability based on a comprehensive calculation that is obtained based on the analysis results;
after determining that the level of the reliability is high, determining whether the electric shock on the patient is necessary or not;
after determining that the electric shock on the patient is necessary, and after determining the level of reliability is high, instructing, as a second procedure to be performed on the patient, an implementation of the electric shock at a timing after the first procedure related to cardiopulmonary resuscitation ends; and
after determining that the electric shock on the patient is not necessary, and after determining the level of reliability is high, instructing, as the second procedure, a continuation of a procedure based on cardiopulmonary resuscitation.

2. The method according to claim 1, wherein, in a process of executing the analysis of the electrocardiogram in each of the analysis zones, the analysis includes detecting in the electrocardiogram in each of the analysis zones whether or not (i) a first waveform is present indicating that the electric shock is necessary or (ii) a second waveform is present indicating that the electric shock is not necessary, and
wherein, based on a number of detections of the first waveform or the second waveform, the determination whether the electric shock on the patient is necessary or not is executed, and the reliability of the determination is calculated.

3. The method according to claim 1, further comprising:
classifying a life-saving procedure state of the patient in each of the analysis zones based on a noise component contaminating the electrocardiogram,
wherein, based on the classified life-saving procedure state of the patient in each of the analysis zones, and the result of the analysis of the electrocardiogram in each of the analysis zones, the determination whether the electric shock on the patient is necessary or not is executed, and the reliability of the determination is calculated.

4. The method according to claim 3, wherein the life-saving procedure state of the patient is classified into:
a state of during procedure in which the first procedure is performed on the patient;
a state of during interruption of procedure in which the first procedure is interrupted; and
a state which includes both the state of during procedure and the state of during interruption of procedure.

5. The method according to claim 4, wherein the first procedure includes chest compression.

6. The method according to claim 5, wherein the life-saving procedure state of the patient is classified based on at least one of: a thoracic impedance; a frequency characteristic of the electrocardiogram; an amplitude of the electrocardiogram; an amplitude of a capnograph; and a signal acquired from an electrode attached to an operator who performs the chest compression.

7. The method according to claim 4, wherein the first procedure includes artificial ventilation.

8. The method according to claim 7, wherein the life-saving procedure state of the patient is classified based on at least one of a thoracic impedance and a capnograph.

9. The method according to claim 4, wherein the reliability of the determination is calculated based on reliability determination information including at least one of:
information indicating whether or not the electrocardiogram has an analysis zone, which is classified as the state of during interruption of procedure;
information indicating whether or not results of analysis in a plurality of analysis zones, which are classified as the state of during procedure, coincide with each other; and
information indicating whether or not, in all analysis zones, an amplitude of the electrocardiogram is within a preset measurable range.

10. The method according to claim 5, wherein the reliability of the determination is calculated based on reliability determination information including at least one of:
information indicating whether or not a period of the chest compression is constant; and
information indicating whether or not a large variation exists in a result of frequency analysis of the electrocardiogram during the chest compression.

11. The method according to claim 3, wherein, the second procedure includes at least one of:
the implementation of electric shock;
the continuation of a procedure based on cardiopulmonary resuscitation;
a check of a pulse; and
an implementation of electrocardiogram analysis.

12. The method according to claim 3, further comprising:
after a process of instructing the second procedure to be performed on the patient,
executing analysis of an electrocardiogram of the patient which is measured while instructing the second procedure;
when a procedure determined from a result of the analysis coincides with the second procedure, continuing instructing the second procedure; and
when a procedure determined from a result of the analysis does not coincide with the second procedure, changing the second procedure to a third procedure.

13. The method according to claim 12, wherein the third procedure includes at least one of an abort of electric shock, and an implementation of reanalysis.

14. The method according to claim 3, wherein, in the electrocardiogram divided into the analysis zones, the electrocardiogram measured in a latest time period and contained in latest zones of the analysis zones is set as an analysis target.

15. The method according to claim 1, wherein the reliability of the determination is calculated based on the result of the analysis of the electrocardiogram in each of the analysis zones, which includes a total number of the analysis zones.

16. The method according to claim 1, further comprising:
when determining that the level of the reliability is low, executing an analysis of an electrocardiogram that is obtained in interruption of chest compression,
determining whether electric shock on the patient is necessary or not in a result of the analysis of the electrocardiogram that is obtained in the interruption of the chest compression,
when determining the electric shock on the patient is necessary, instructing an implementation of the electric shock, and
when determining the electric shock on the patient is not necessary, instructing a continuation of cardiopulmonary resuscitation.

17. The method according to claim 1, wherein the only one result of the analysis in each of the divided analysis zones is obtained exclusively using unfiltered data.

18. The method according to claim 1, wherein
when a number of analysis zones analyzed is less than a given number of analysis zones a low reliability is calculated, and
when an analysis zone exceeds a measurable range and is omitted to cause a number of analysis zones analyzed to be less than the given number of analysis zones a low reliability is calculated.

19. A defibrillator with a function of analyzing an electrocardiogram, the defibrillator analyzing the electrocardiogram during a procedure based on cardiopulmonary resuscitation, the defibrillator comprising:
a cardiopulmonary resuscitation instructing section which is configured to instruct an operator on a start and end of the procedure based on cardiopulmonary resuscitation;
an electrocardiogram analyzing section which is configured to:
divide an electrocardiogram of a patient into a plurality of analysis zones;
execute analysis of the electrocardiogram in each of the divided analysis zones to obtain, as analysis results, only one result of the analysis in each of the divided analysis zones of the electrocardiogram obtained during the procedure based on cardiopulmonary resuscitation; and
based on the analysis results:
execute a determination of whether electric shock on the patient is necessary or not, and
calculate a reliability of the determination;
a cardiopulmonary resuscitation post-procedure instructing section which is configured, to,
determine a level of the reliability based on a comprehensive calculation that is obtained based on the analysis results,
after determining that the level of the reliability is high, determine whether the electric shock on the patient is necessary or not,
after determining that the electric shock on the patient is necessary, and after determining the level of reliability is high, instruct the operator on an implementation of the electric shock at a timing after the procedure based on cardiopulmonary resuscitation ends, and
after determining that the electric shock on the patient is not necessary, and after determining the level of reliability is high, instructing the operator on an implementation of cardiopulmonary resuscitation.

20. The defibrillator according to claim 19, wherein the electrocardiogram analyzing section is configured to detect whether or not a first waveform indicating that the electric shock is necessary or a second waveform indicating that the electric shock is not necessary is contained in the electrocardiogram in each of the analysis zones, and
based on a number of detections of the first waveform or the second waveform, the electrocardiogram analyzing section is configured to execute the determination whether the electric shock on the patient is necessary or not, and calculate the reliability of the determination.

21. The defibrillator according to claim 19, wherein the electrocardiogram analyzing section is configured to classify a life-saving procedure state of the patient in each of the analysis zones based on a noise component contaminating the electrocardiogram, and
based on the classified life-saving procedure state of the patient in each of the analysis zones, and the result of the analysis of the electrocardiogram in each of the analysis zones, the electrocardiogram analyzing section is configured to execute the determination whether the electric shock on the patient is necessary or not, and calculate the reliability of the determination.

22. The defibrillator according to claim 19, wherein the reliability of the determination is calculated based on the result of the analysis of the electrocardiogram in each of the analysis zones, which includes a total number of the analysis zones.

23. The defibrillator according to claim 19, wherein the only one result of the analysis in each of the divided analysis zones is obtained exclusively using unfiltered data.

24. The defibrillator according to claim 19, wherein the electrocardiogram analyzing section is further configured to cause calculation of high reliability when a number of analysis zones analyzed is greater than a given number of analysis zones, and to cause calculation of low reliability when
a number of analysis zones analyzed is less than the given number of analysis zones, or
when an analysis zone exceeds a measurable range and is omitted to cause a number of analysis zones analyzed to be less than the given number of analysis zones.

* * * * *